United States Patent [19]

Naik et al.

[11] Patent Number: 4,764,529

[45] Date of Patent: * Aug. 16, 1988

[54] PESTICIDAL POUR-ON FORMULATIONS PARTICULARLY EFFECTIVE AGAINST ACARINES AND INSECTS

[75] Inventors: Arundev H. Naik, Leverkusen; Wilhelm Stendel, Wuppertal; Herbert Voege, Leverkusen, all of Fed. Rep. of Germany

[73] Assignee: Bayer Aktiengesellschaft, Leverkusen, Fed. Rep. of Germany

[ * ] Notice: The portion of the term of this patent subsequent to Mar. 15, 2005 has been disclaimed.

[21] Appl. No.: 776,949

[22] Filed: Sep. 17, 1985

Related U.S. Application Data

[63] Continuation of Ser. No. 470,022, Feb. 25, 1983, abandoned.

[30] Foreign Application Priority Data

Mar. 9, 1982 [DE] Fed. Rep. of Germany ....... 3208334

[51] Int. Cl.$^4$ ............................................. A61K 31/215
[52] U.S. Cl. .................................................... 514/531
[58] Field of Search ......................................... 514/531

[56] References Cited

U.S. PATENT DOCUMENTS

| | | | |
|---|---|---|---|
| 4,020,181 | 4/1977 | Blackman et al. | 514/531 |
| 4,297,366 | 10/1981 | Fuchs et al. | 514/531 |
| 4,325,969 | 4/1982 | Brown | 514/531 |
| 4,341,760 | 7/1982 | Matthewson | 514/531 |
| 4,607,050 | 8/1986 | Kieran et al. | 514/531 |

FOREIGN PATENT DOCUMENTS 2088212 6/1982 United Kingdom .

*Primary Examiner*—Sam Rosen
*Attorney, Agent, or Firm*—Sprung Horn Kramer & Woods

[57] ABSTRACT

The invention relates to pesticidal (e.g. pyrethroid) pour-on formulations prepared on an aqueous basis; and also includes the method of combatting pests and parasites of warm-blooded animals, particularly acarines and insects by applying said pour-on formulations to the animals.

4 Claims, No Drawings

PESTICIDAL POUR-ON FORMULATIONS PARTICULARLY EFFECTIVE AGAINST ACARINES AND INSECTS

This is a continuation of application Ser. No. 470,022, filed 2/25/83, now abandoned.

The invention relates to pour-on formulations of pesticidal active compounds which have, in particular, an action on acarines and insects, and the preparation and use of the pesticidal pour-on formulations.

Pesticidal pour-on formulations are characterised in that they contain the active compound dissolved, emulsified or suspended in a suitable solvent or solvent mixture which is tolerated by skin, if appropriate with the addition of other auxiliaries, and can be applied with the aid of a suitable device (for example with the aid of a measuring beaker, a spray bottle or a metering syringe) to the skin and/or coat of the animal to be treated.

Pour-on formulations of insecticides and anthelmintic agents are already known in veterinary medicine (in this context, see Rogoff, W. M. and Kohler, P. H., J.Econ.Ent. 53, 814–817 (1960)). Farmers, chemists and veterinarians are familiar with the expression "pour-on formulation" or "spot-on formulation". Such a formulation is a liquid product which is suitable for so-called "pour-on application" and is poured onto the skin (pour-on treatment).

For example, systemic phosphoric acid esters, such as Ruelene, trichlorphon, fenthion and others, which have a very powerful insecticidal action are used in the form of pour-on formulations for combating warble-fly larvae.

However, it was not hitherto possible to combat ticks with the necessary success by this method. Although such pour-on formulations displayed a certain action, this is by far inadequate. Ticks are therefore combated, as before, in the conventional manner by means of dipping baths or by spraying with aqueous active compound emulsions or suspensions.

It has already been found that pour-on formulations can be effective against ticks if they are formulated with organic solvents and spreading oils.

According to the invention, pour-on formulations can surprisingly also be prepared on an aqueous basis, and may then have an even better action than the pour-on formulations on an oily basis hitherto described.

The invention accordingly relates to pesticidal pour-on formulations consisting of 0.05 to 30 parts by weight of an active compound, 0.5 to 90 parts by weight of a surface-active agent, 0 to 99 parts by weight of water, 0 to 95 parts by weight of a water-miscible solvent and, if appropriate, up to 10 parts by weight of auxiliaries.

The pesticidal formulations according to the invention preferably consist of 0.1 to 10 parts by weight of a pesticidal active compound, 1 to 30 parts by weight of a surface-active agent, 20 to 70 parts by weight of a water-miscible solvent, 5 to 50 parts by weight of water and, if appropriate, up to 5 parts by weight of auxiliaries.

Those pesticidal formulations which contain a non-ionic, water-soluble, surface-active agent having an HLB value (hydrophilic/lipophilic balance) of greater than 10 are particularly suitable for combating harmful pests and nuisance pests.

The pour-on formulations according to the invention are inexpensive and simple to prepare. Like conventional formulations, they are suitable for direct use, without dilution. However, if necessary, they can be diluted in any desired ratio with water or water-miscible solvents, in order to vary the dose/volume/body surface area relationship or other properties.

The pesticidal formulations according to the invention can contain auxiliaries, such as preservatives, antioxidants, stabilisers, colorants, antifoaming agents, adhesives and synergistic agents.

Suitable active compounds are hydrophilic or lipophilic pesticides.

The active compounds which follow are particularly suitable for the pesticidal formulations according to the invention:

Pyrethroids, for example:
(α-Cyano-4-fluoro-3-phenoxy)-benzyl 3-[2-(4-chlorophenyl)-2-chlorovinyl]-2,2-dimethyl-cyclopropanecarboxylate (flumethrin); α-cyano-3-phenoxybenzyl (±)-cis/trans-3-(2,2-dibromovinyl)-2,2-dimethylcyclopropanecarboxylate; (α-cyano-3-phenoxy)-benzyl 2,2-dimethyl-3-(2,2-dichlorovinyl)-cyclopropanecarboxylate; 3-phenoxybenzyl (±)-cis/-trans-3-(2,2-dichlorovinyl)-2,2-dimethylcyclopropanecarboxylate; α-cyano-3-phenoxy-benzyl α-(p-Cl-phenyl)isovalerate; cyano-(3-phenoxyphenyl)-methyl 3,3-spiro[cyclopropane-1,1-(1H)-indene]-2-carboxylate; 5-benzyl-3-furylmethyl (±)-cis/trans-chrysanthemate; 2-methyl-4-oxo-3-(penta-2,4-dien-1-yl)-cyclopent-2-en-1-yl chrysanthemate, pyrethrin II, cinerin I and II, jasmolin I and II; cyano-(4-fluoro-3-phenoxyphenol)-methyl 3-2,2-dichloroethenyl)-2,2-dimethyl-cyclopropanecarboxylate; pentafluorophenyl-methyl 3-(2,2-dichloroethenyl)-2,2-dimethyl-cyclopropanecarboxylate and other pyrethroids which are known from the literature (for example those described in European Patent Application No. 345).

Carbamates, for example:
2-Isopropoxyphenyl methylcarbamate and 1-naphthyl N-methylcarbamate.

Organophosphates, for example:
O-Ethyl O-(quinol-8-yl)benzene-thiophosphonate; O,O-diethyl O-(3-chloro-4-methyl-7-coumarinyl)phosphorothioate; O,O-diethyl α-cyanobenzylidene-amino-oxyphosphonothioate; O,O-diethyl 0,4-bromo-2,5-dichlorophenyl phosphorothioate; O,O,O',O'-tetraethyl S,S'-methylene-di(phosphorodithioate); 2,3-p-dioxane-dithiol-S,S-bis-(O,O-diethyl phosphorodithioate); 2-chloro-1-(2,4-dichlorophenyl)-vinyl diethyl phosphate and O,O-dimethyl O-(3-methyl-4-n-methylthiophenyl)thionophosphate.

Amidines, for example:
3-Methyl-2-[2,4-dimethyl-phenylimino]-thiazoline; 2-(4-chloro-2-methylphenylimino)-3-methylthiazolidine; 2-(4-chloro-2-methylphenylimino)-3-(isobutyl-1-enyl)-thiazolidine and N,N-di-(2,4-xylyliminomethyl)-methylamine.

Benzenephenylureas, for example:
1-(4-Chlorophenyl)-3-(2,6-difluorobenzoyl)-urea and 1-(2-chloro-benzoyl)-3-(4-trifluoromethoxyphenyl)-urea.

Chlorinated hydrocarbons, for example:
1,2,3,4,5,6,-γ-Hexachlorocyclohexane.

Pheromones, juvenile hormones, anti-juvenile hormones, attractants and repellants can also be used as active constituents of the pesticidal pour-on formulations.

Preferred surface-active agents according to the invention are non-ionic, water-soluble emulsifiers having an HLB (hydrophilic/lipophilic balance value) of greater than 10.

Emulvin W ® (Bayer AG), alkylaryl polyglycol ether; Emulgator NP 10 ® (Bayer AG), alkylaryl polyglycol ether; Emulgator SZZ 14 ® (Bayer AG), alkylaryl polyglycol ether; Emulgator SZZ 1166 B ® (Bayer AG), alkylaryl polyglycol ether; Emulgator SZZ 1166 C ® (Bayer Ag), alkylaryl polyglycol ether; Renex 678 ® (Atlas Chemical Industries), polyoxyethylene alkylaryl ether; Tween 40 ® (Atlas), polyoxyethylene sorbitan monopalmitate; Myrj 53 ® (Atlas), polyoxyethylene stearate; Atlas G 3707 ®, polyoxyethylene lauryl ether; Atlas G 3920 ®, polyoxyethylene oleyl ether; Atlas G 9046 T ®, polyoxyethylene mannitan monolaurate; Emulgator 1371 B ® (Bayer AG), alkyl polyglycol ether; Emulgator 1736 ® (Bayer AG), alkyl polyglycol ether (oleyl polyglycol ether); Emulgator OX ® (Bayer AG), alkyl polyglycol ether ((dodecyl polyglycol ether); Ninox BM-2 ® (Stepan Chemical Co.), ethoxylated nonylphenol; Triton X-100° (Rohm and Haas Co.), isooctylphenol polyethoxyethanol; Cremophor EL ®.

The water-miscible solvents mentioned below are preferably suitable for the preparation of the pesticidal formulations according to the invention: methanol, ethanol, propanol, particularly preferably isopropanol, dimethyl sulphoxide, dimethylformamide, glycerols, ethylene glycol monomethyl ether, ethylene glycol monomethyl ether-acetate (methyl-Cellosolv acetate), ethylene glycol monoethyl ether, diethylglycol, diethylene glycol monomethyl ether (methoxyethoxyethanol, methyl-Carbitol), diethylene glycol monoethyl ether (ethyldiglycol, Carbitol) diethylene glycol monoethyl ether-acetate, diethylene glycol dimethyl ether, diethylene glycol diethyl ether (diethyl-Carbitol) polyethylene glycols, propylene glycols, polypropylene glycols and ketones, such as acetone and methyl ethyl ketone.

Formulations

The formulations according to the invention are prepared by dissolving the active compound in an emulsifier or in an emulsifier/solvent mixture while warming, if necessary, and by adding the required amount of water, while stirring. No particular homogenising device is necessary.

The examples which follow of new formulations are intended to illustrate these, but not to restrict the invention.

EXAMPLE 1

| | | |
|---|---|---|
| Active compound: | (α-Cyano-4-fluoro-3-phenoxy)-benzyl 3-[2-(4-chlorophenyl)-2-chlorovinyl]-2,2-dimethylcyclopropane-carboxylate | 0.5 g |
| Surfactant: | Emulvin W ® (alkylaryl polyglycol ether) | 3.0 g |
| Water: | | to 100 ml |

EXAMPLE 2

| | | |
|---|---|---|
| Active compound: | as Example 1 | 2.5 g |
| Surfactant: | as Example 1 | 15.0 g |
| Solvent: | Polyethylene glycol (molecular weight 200) | 15.0 g |
| Water: | | to 100 ml |

EXAMPLE 3

| | | |
|---|---|---|
| Active compound: | as Example 1 | 1.0 g |
| Surfactant: | Emulsifier NP 10 ® (alkylaryl polyglycol ether) | 20.0 g |
| Water: | | to 100 ml |

EXAMPLE 4

| | | |
|---|---|---|
| Active compound: | as Example 1 | 5.0 g |
| Surfactant: | Emulsifier SZZ 14 ® | 20.0 g |
| Solvent: | Isopropanol | to 100 ml |
| Water: | | 5.0 g |

EXAMPLE 5

| | | |
|---|---|---|
| Active compound: | 2-Isopropoxyphenyl methylcarbamate | 5.0 g |
| Surfactant: | Triton X-100 ® (isooctylphenol polyethoxyethanol) | 30.0 g |
| Solvent: | Ethanol | 30.0 g |
| Water: | | to 100 ml |

EXAMPLE 6

| | | |
|---|---|---|
| Active compound: | 3-Methyl-2-[2,4-dimethylphenylimino]-thiazoline | 3.0 g |
| Surfactant: | Renex 678 ® (polyoxyethylenealkylaryl ether) | 30.0 g |
| Water: | | to 100 ml |

EXAMPLE 7

| | | |
|---|---|---|
| Active compound: | O,O—Dimethyl O—(3-methyl-4-n-methylthiophenyl) thionophosphate | 1.0 g |
| Surfactant: | as Example 1 | 20.0 g |
| Solvent: | Isopropanol | 18.0 g |
| Water: | | to 100 ml |

EXAMPLE 8

| | | |
|---|---|---|
| Active compound: | O,O—Diethyl α-cyanobenzylidene-amino-oxyphosphonothioate | 5.0 g |
| Surfactant: | as Example 1 | 30.0 g |
| Solvent: | Isopropanol | to 100 ml |
| Water | | 5.0 g |

EXAMPLE 9

| | | |
|---|---|---|
| Active compound: | Pentafluorophenyl-methyl 3-(2,2-dichloroethenyl)-2,2-dimethyl-cyclopropanecarboxylate | 0.5 g |
| Solvent: | Polyethylene glycol (molecular weight 400) | 20.0 g |
| Surfactant: | Emulvin W ® (alkylaryl polyglycol ether) | 12.5 g |

-continued

| | | |
|---|---|---|
| Auxiliary: | Xanthan gum | 0.5 g |
| | Benzyl alcohol | 2.0 g |
| Water: | | to 100 ml |

EXAMPLE 10

| | | |
|---|---|---|
| Active compound: | Cyano-(4-fluoro-3-phenoxy-phenyl)-methyl 3-(2,2-dichloro-ethenyl)-2,2-dimethyl-cyclo-propanecarboxylate | 2.0 g |
| Surfactant: | Emulgator SZZ 1147 ® (alkylaryl polyglycol ether) | 20.0 g |
| Water: | | 5.0 g |
| Solvent: | Ethylene glycol monomethyl ether | to 100 ml |

The activity of the formulations claimed can be demonstrated by the following experiment:

Cattle were infested with larvae of the cattle tick Boophilus microplus, Biarra strain. The activity was determined by counting the number of ticks which laid fertile eggs in comparison with the untreated group. The result can be seen from the table which follows.

| | | Number of ticks per animal which laid fertile eggs | |
|---|---|---|---|
| Group | Dose | −2 to 0 days | 0 to 21 days |
| Control | — | 940 | 3,032 |
| Pour-on formulation Example 1 | 1 mg/kg | 1,737 | 0 |
| Pour-on formulation Example 2 | 1 mg/kg | 552 | 0 |
| Pour-on formulation Example 4 | 1 mg/kg | 657 | 0 |

The table shows the activity of the pour-on/spot-on formulations according to the invention even at the low dosage of the active compound of 1 mg/kg of body weight.

What is claimed is:

1. A method of combating pests and parasites of warm-blooded animals which comprises applying to said animals a pesticide- or parasite-combating effective amount of a pesticide pour-on formulation consisting essentially of 0.5–5 parts by weight of a pyrethroid selected from the group consisting of α-cyano-4-fluoro-3-phenoxy-benzyl-3-(2-(4-chlorphenyl)-2-chlorvinyl)-2,2-dimethyl-cyclopropane carboxylate, pentafluror-phenyl-methyl-3-(2,2-dichloroethenyl)-2,2-dimethyl-cyclopropanecarboxylate, α-cyano(4-fluoro-3-phenoxy-phenyl)-methyl-3-(2,2-dichloroethenyl)-2,2-dichloroethenyl)-2,2-dimethyl-cyclopropanecarboxylate, 3–20 parts by weight of a alkylaryl-polyglycolether surfactant, 0–73 parts by weight of a water-miscible solvent selected from the group consisting of isopropanol, polyethyleneglycol, ethyleneglycol-monomethyl-ether, 0–2.5 parts by weight of auxiliaries selected from the group consisting of xanthan gum and benzyl-alcohol and the rest being water, said water being at least 5 parts by weight, said formulation prepared by dissolving the pyrethroid in the surfactant, the solvent and the auxiliaries and then adding the water.

2. A method according to claim 1, containing (α-cyano-4-fluoro-3-phenoxy)-benzyl 3-[2-(4-chloro-phenyl)-2-chlorovinyl]-2,2-dimethyl-cyclopropanecarboxylate as the pyrethroid.

3. A method according to claim 1, containing pentafluorophenyl-methyl-3-(2,2-dichloroethenyl)-2,2-dimethyl-cyclopropanecarboxylate as the pyrethroid.

4. A method according to claim 1, containing cyano-(4-fluoro-3-phenoxy-phenyl)methyl-3-2,2-dichloroethenyl)-2,2-dimethyl-cyclopropanecarboxylate as the pyrethroid.

* * * * *